US012577276B2

(12) United States Patent
Fiedler et al.

(10) Patent No.: US 12,577,276 B2
(45) Date of Patent: Mar. 17, 2026

(54) IMMUNOGLOBULIN BINDING PROTEINS FOR AFFINITY PURIFICATION

(71) Applicant: Navigo Proteins GmbH, Halle/Saale (DE)

(72) Inventors: Erik Fiedler, Halle/Saale (DE); Mathias Kahl, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 1213 days.

(21) Appl. No.: 17/430,238

(22) PCT Filed: Jan. 31, 2020

(86) PCT No.: PCT/EP2020/052438
§ 371 (c)(1),
(2) Date: Aug. 11, 2021

(87) PCT Pub. No.: WO2020/157281
PCT Pub. Date: Aug. 6, 2020

(65) Prior Publication Data
US 2022/0112236 A1    Apr. 14, 2022

(30) Foreign Application Priority Data

Feb. 1, 2019    (EP) ..................................... 19154972
Aug. 26, 2019    (EP) ..................................... 19193552

(51) Int. Cl.
*C07K 14/305* (2006.01)
*C07K 1/22* (2006.01)

(52) U.S. Cl.
CPC .............. *C07K 1/22* (2013.01); *C07K 14/305* (2013.01)

(58) Field of Classification Search
CPC ............................... C07K 1/22; B01D 15/3809
See application file for complete search history.

(56) References Cited

U.S. PATENT DOCUMENTS

| | | | | | |
|---|---|---|---|---|---|
| 11,014,967 | B2 * | 5/2021 | Knick | .................... | C07K 14/31 |
| 11,230,576 | B2 * | 1/2022 | Knick | .................. | C07K 16/065 |
| 11,548,929 | B2 * | 1/2023 | Fiedler | .................. | B01J 20/289 |
| 11,779,860 | B2 * | 10/2023 | Fiedler | .............. | B01D 15/3809 |
| | | | | | 210/635 |

FOREIGN PATENT DOCUMENTS

| | | | | | |
|---|---|---|---|---|---|
| EP | | 2 518 151 A1 | 10/2012 | | |
| WO | WO 2016/079033 | | 5/2016 | | |
| WO | WO 2017/009421 | | 1/2017 | | |
| WO | WO-2017009421 A1 * | | 1/2017 | .............. | C07K 1/22 |
| WO | WO-2018029157 A1 * | | 2/2018 | ........ | B01D 15/3804 |
| WO | WO-2019030156 A1 * | | 2/2019 | ........ | B01D 15/3809 |
| WO | WO 2019/152318 A1 | | 8/2019 | | |

OTHER PUBLICATIONS

Hober, et al J. Chromatography B 848 p. 40 (Year: 2007).*
Tsukamoto et al J. Biol. Engineering 8:15 (9 pages) (Year: 2014).*
Yu et al PLOS One vol. 8 issue 2 (11 pages) (Year: 2013).*
International Search Report corresponding to International Patent Application No. PCT/EP2020/052438 dated Mar. 19, 2020.
Written Opinion corresponding to International Application No. PCT/EP2020/052438 dated Aug. 6, 2020.

* cited by examiner

*Primary Examiner* — Julie Wu

(57) ABSTRACT

The present invention relates to immunoglobulin (Ig) binding proteins comprising one or more domains. The invention further relates to affinity matrices comprising the Ig binding proteins of the invention. The invention also relates to a use of these Ig binding proteins or affinity matrices for affinity purification of immunoglobulins and to methods of affinity purification using the Ig binding proteins of the invention.

14 Claims, 5 Drawing Sheets

Specification includes a Sequence Listing.

IMMUNOGLOBULIN BINDING PROTEINS FOR AFFINITY PURIFICATION

FIELD OF THE INVENTION

The present invention relates to immunoglobulin (Ig) binding proteins comprising one or more domains. The invention further relates to affinity matrices comprising the Ig binding proteins of the invention. The invention also relates to a use of these Ig binding proteins or affinity matrices for affinity purification of immunoglobulins and to methods of affinity purification using the Ig binding proteins of the invention.

BACKGROUND OF THE INVENTION

Many biotechnological and pharmaceutical applications require the removal of contaminants from a sample containing antibodies. An established procedure for capturing and purifying antibodies is affinity chromatography using the bacterial cell surface Protein A from *Staphylococcus aureus* as selective ligand for immunoglobulins (see, for example, review by Huse et al., J. Biochem. Biophys. Methods 51, 2002: 217-231). Wild-type Protein A binds to the Fc region of IgG molecules with high affinity and selectivity. Variants of Protein A with improved properties such as alkaline stability are available for purifying antibodies and various chromatographic matrices comprising Protein A ligands are commercially available. However, currently available Protein A based chromatography matrices show a loss of binding capacity for immunoglobulins following exposure to alkaline conditions.

TECHNICAL PROBLEMS UNDERLYING THE INVENTION

Most large scale production processes for antibodies or Fc-containing fusion proteins use Protein A for affinity purification. However, due to limitations of Protein A applications in affinity chromatography there is a need in the art to provide novel Ig binding proteins with improved properties that specifically bind to immunoglobulins in order to facilitate affinity purification of immunoglobulins. To maximally exploit the value of the chromatographic matrices comprising Ig binding proteins it is desirable to use the affinity ligand matrices multiple times. Between chromatography cycles a thorough cleaning procedure is required for sanitization and removal of residual contaminants on the matrix. In this procedure, it is general practice to apply alkaline solutions with high concentrations of NaOH to the affinity ligand matrices. Wild-type Protein A domains cannot withstand such harsh alkaline conditions for an extended time and quickly lose binding capacity for immunoglobulin. Further, for a repeated use of affinity ligand matrices, a cleaning step under harsh acidic conditions is required.

Accordingly, there is an ongoing need in this field to obtain novel proteins capable of binding proteins comprising an Fc sequence and to withstand the harsh cleaning conditions applied in affinity chromatography.

The present invention provides Ig binding proteins that are particularly well-suited for affinity purification of immunoglobulins. In particular, the Ig binding proteins of the invention have several advantages. One significant advantage of the Ig binding proteins of the invention is their improved stability at high pH for a prolonged time period without reducing the Ig binding capacities in combination with high dynamic binding capacities.

The above overview does not necessarily describe all problems solved by the present invention.

SUMMARY OF THE INVENTION

An aspect of the present invention is to provide an Ig binding protein suitable for affinity purification.

[1] This is achieved with an Ig binding protein comprising one or more Ig binding domains, wherein at least one domain comprises or consists of an amino acid sequence of any of SEQ ID NO: 1 (cs50), SEQ ID NO: 2 (cs52), SEQ ID NO: 3 (cs58), SEQ ID NO: 4 (cs59), SEQ ID NO: 5 (cs60), SEQ ID NO: 6 (cs51), SEQ ID NO: 7 (cs56), SEQ ID NO: 8 (cs54), or SEQ ID NO: 10 (cs55), or an amino acid sequence with at least 95% identity to any of SEQ ID NO: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 10.

[2] The Ig binding protein according to [1], wherein said domain comprises the amino acid sequence as set forth in SEQ ID NO: 1 (cs50) or a sequence at least 95% identical thereto.

[3] The Ig binding protein according to [1], wherein said domain comprises the amino acid sequence as set forth in SEQ ID NO: 7 (cs56) or a sequence at least 95% identical thereto, or wherein said domain comprises the amino acid sequence as set forth in SEQ ID NO: 10 (cs55) or a sequence at least 95% identical thereto.

[4] The Ig binding protein according to [3], wherein said domain comprises the amino acid sequence as set forth in SEQ ID NO: 8 (cs54) or SEQ ID NO: 9 (cs57).

[5] The Ig binding protein according to [1]-[4], wherein the protein comprises 2, 3, 4, 5, 6, 7, or 8 domains linked to each other.

[6] The Ig binding protein according to [5], wherein the protein is a homo-multimer or a hetero-multimer.

[7] The Ig binding protein according to [6], wherein one or more domains are linked to each other directly or with one or more linkers.

[8] The Ig binding protein according to any one of [1]-[7], wherein said protein binds to IgG$_1$, IgG$_2$, IgG$_4$, IgM, IgA, Ig fragments, Fc fragments, or Fab fragments.

[9] The Ig binding protein according to any one of [1]-[8], wherein the protein is immobilized to a solid support.

[10] An affinity separation matrix comprising the Ig binding protein according to any one of [1]-[9] coupled to said affinity separation matrix.

[11] Use of the Ig binding protein according to any one of [1]-[9] or of the affinity separation matrix according to [10] for affinity purification of any protein with affinity to the Ig binding protein.

[12] A method of affinity purification of a protein comprising an Ig sequence, the method comprising:
(a) providing a liquid that contains protein comprising an Ig sequence;
(b) providing an affinity separation matrix according to [10];
(c) contacting said affinity separation matrix with the liquid under conditions that permit binding of the at least one Ig binding protein according to any one of [1]-[9] to a protein comprising an Ig sequence; and
(d) eluting said protein comprising an Ig sequence from said affinity purification matrix.

[13] The method according to [12] wherein in step (d) wherein more than 90% of the protein comprising the Ig sequence is eluted from the Ig binding protein according to any of [1]-[9].

[14] The method according to [12]-[13], comprising the additional step of (e) cleaning the affinity purification matrix with an alkaline cleaning liquid.

[15] The method according to [14], wherein the Ig-binding capacity of the Ig binding protein is at least 70% of the Ig binding capacity before the incubation under alkaline conditions.

This summary of the invention does not necessarily describe all features of the present invention. Other embodiments will become apparent from a review of the ensuing detailed description.

BRIEF DESCRIPTION OF THE FIGURES

FIGS. 1A and 1B. Amino acid sequences of novel Ig binding proteins. The numbers in the top row refer to the corresponding amino acid position in the Ig binding protein.

FIG. 1A. Consensus amino acid sequence of SEQ ID NO: 17 and amino acid sequences of SEQ ID NOs: 1-6. Variable amino acids in positions 3, 9, 40, 43, and 46 are shown in grey. SID: SEQ ID NO:, FIG. 1B. Consensus amino acid sequence of SEQ ID NO: 18 and amino acid sequences of SEQ ID NOs: 7-10. Variable amino acids in positions 2, 4, 7, 40, 46, and 53 are shown in grey. SID: SEQ ID NO:, FIG. 2. Immobilization on PRAESTO® Pure 85 brand chromatography medium (Ecolab Purolite Resins, St. Paul, Minnesota, United States of America). Coupling efficiency of Ig binding proteins on Epoxy-matrix PRAESTO® Pure 85 brand chromatography medium (Ecolab Purolite Resins, St. Paul, Minnesota, United States of America). Y-axis: coupled amount of protein to epoxy-matrix in mg/ml.

FIG. 4A. Analysis of the alkaline stability of Ig binding proteins, compared to MABSELECT SURE® brand chromatography medium (Cytiva Bioprocess R&D AB, Uppsala, Sweden). Y-axis: remaining IgG binding activity in % after 24 h 0.5 M NaOH incubation.

DETAILED DESCRIPTION OF THE INVENTION

Figure 2:
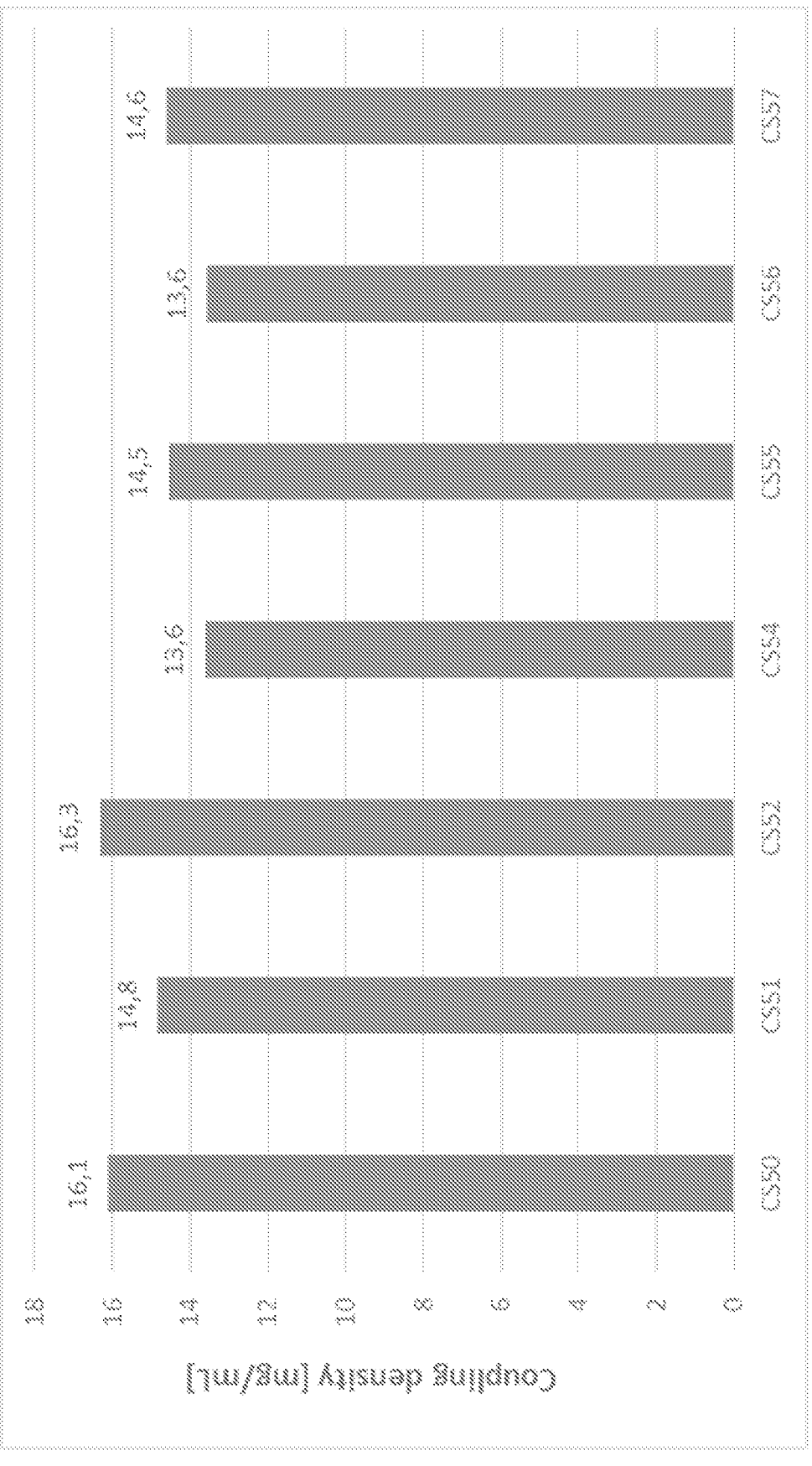

Before the present invention is described in detail below, it is to be understood that this invention is not limited to the particular methodology, protocols and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are consistent with the definitions provided in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

The term "about", as used herein, encompasses the explicitly recited amounts as well as deviations therefrom of ±10%. More preferably, a deviation 5% is encompassed by the term "about".

Several documents (for example: patents, patent applications, scientific publications, manufacturer's specifications etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, is a part of this specification.

In the context of the present invention, the term "Ig binding protein" or "immunoglobulin-binding protein" is used to describe proteins that are capable to specifically bind to an immunoglobulin. The "immunoglobulin" or "Ig" as understood herein can include, but is not necessarily limited to, mammalian IgG, such as for example human $IgG_1$, human $IgG_2$, human $IgGa_4$, mouse IgG, rat IgG, goat IgG, bovine IgG, guinea pig IgG, rabbit IgG; human IgM, human IgA; and an immunoglobulin fragment comprising a Fc region (also referred to as "Fc fragment" or "Fc") and/or an immunoglobulin fragment comprising a Fab region (also referred to as "Fab fragment" or "Fab"). The Ig binding proteins are capable of binding to entire immunoglobulins, and to Ig fragments comprising a Fc region and/or Ig fragments comprising a Fab region. The definition "immunoglobulin" as understood herein includes fusion proteins comprising an immunoglobulin, fragment of an immunoglobulin comprising a Fc region (Fc fragment), fragment of an immunoglobulin comprising a Fab region (Fab fragment), fusion proteins comprising a fragment of an immunoglobulin comprising a Fc region, fusion proteins comprising a fragment of an immunoglobulin comprising a Fab region, conjugates comprising an Ig or an Ig fragment comprising a Fc region (Fc fragment), and conjugates comprising an Ig fragment comprising a Fab region (Fab fragment).

The term "binding" according to the invention preferably relates to a specific binding. "Specific binding" means that an Ig binding protein or an Ig binding domain binds stronger to an immunoglobulin for which it is specific compared to the binding to another non-immunoglobulin target.

The term "binding activity" refers to the ability of an Ig binding protein of the invention to bind to immunoglobulin. For example, the binding activity can be determined before and/or after alkaline treatment. The binding activity can be determined for an Ig binding protein or for an Ig binding protein coupled to a matrix, i.e. for an immobilized binding protein. The term "artificial" refers to an object that is not naturally occurring, i.e. the term refers to an object that has been produced or modified by man. For example, a polypeptide or polynucleotide sequence that has been generated by man (e.g. for example in a laboratory by genetic engineering, by shuffling methods, or by chemical reactions, etc.) or intentionally modified is artificial.

The term "dissociation constant" or "$K_D$" defines the specific binding affinity. As used herein, the term "$K_D$" (usually measured in "mol/L", sometimes abbreviated as "M") is intended to refer to the dissociation equilibrium constant of the particular interaction between a first protein and a second protein. In the context of the present invention, the term $K_D$ is particularly used to describe the binding affinity between an Ig binding protein and an immunoglobulin. An Ig binding protein of the invention is considered to bind to an immunoglobulin, if it has a dissociation constant $K_D$ to immunoglobulin of at least 1 µM or less, or preferably 100 nM or less, more preferably 50 nM or less, even more preferably 10 nM or less.

The terms "protein" and "polypeptide" refer to any linear molecular chain of two or more amino acids linked by peptide bonds and does not refer to a specific length of the product. Thus, "peptides", "protein", "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-translational modifications of the polypeptide, including without limitation glycosylation, acetylation, phosphorylation, amidation, proteolytic cleavage, modification by non-naturally occurring amino acids and similar modifications which are well-known in the art. Thus, Ig binding proteins comprising two or more protein domains also fall under the definition of the term "protein" or "polypeptides".

The terms "alkaline stable" or "alkaline stability" or "caustic stable" or "caustic stability" (also abbreviated as "cs" herein) refer to the ability of the Ig binding protein of the invention to withstand alkaline conditions without significantly losing the ability to bind to immunoglobulins. The skilled person in this field can easily test alkaline stability by incubating an Ig binding protein with for example sodium hydroxide solutions, e.g., as described in the Examples, and subsequent testing of the binding activity to immunoglobulin by routine experiments known to someone skilled in the art, for example, by chromatographic approaches.

Ig binding proteins of the invention as well as matrices comprising Ig binding proteins of the invention exhibit an "increased" or "improved" alkaline stability, meaning that the molecules and matrices incorporating said Ig binding proteins are stable under alkaline conditions for an extended period of time relative to a reference.

The term "variant" as used herein includes an amino acid sequence of an Ig binding protein or domain that differs from another amino acid sequence by at least one amino acid substitution, deletion or insertion. These modifications may be generated by genetic engineering or by chemical synthesis or chemical reactions carried out by man.

The term "conjugate" as used herein relates to a molecule comprising or essentially consisting of at least a first protein attached chemically to other substances such as to a second protein or a non-proteinaceous moiety.

The term "modification" or "amino acid modification" refers to an exchange, a deletion, or an insertion of an amino acid at a particular position in a polypeptide sequence by another amino acid. Given the known genetic code, and recombinant and synthetic DNA techniques, the skilled scientist can readily construct DNAs encoding the amino acid variants.

The term "substitution" or "amino acid substitution" refers to an exchange of an amino acid at a particular position in a polypeptide sequence by another amino acid. The term "deletion" or "amino acid deletion" refers to the removal of an amino acid at a particular position in a polypeptide sequence.

The term "insertions" or "amino acid insertion" refers to the addition of amino acids to the polypeptide sequence.

Throughout this description, the amino acid residue position numbers are designated as corresponding to those for example in SEQ ID NOs: 1-10.

The term "amino acid sequence identity" refers to a quantitative comparison of the identity (or differences) of the amino acid sequences of two or more proteins. "Percent (%) amino acid sequence identity" or "percent identical" or "percent identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity.

To determine the sequence identity, the sequence of a query protein is aligned to the sequence of a reference protein. Methods for alignment are well-known in the art. Methods for sequence alignment are well known in the art. For example, for determining the extent of an amino acid sequence identity of an arbitrary polypeptide relative to the reference amino acid sequence, the SIM Local similarity program is preferably employed. For multiple alignment analysis, ClustalW as known to someone skilled in the art is preferably used.

The extent of sequence identity is generally calculated with respect to the total length of the unmodified sequence. As used herein, the phrases "percent identical" or "percent (%) amino acid sequence identity" or "percent identity", in the context of two polypeptide sequences, refer to two or more sequences or subsequences that have in some embodiments at least 89.5%, in some embodiments at least 91%, some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments 100% amino acid residue identity, when compared and aligned for maximum correspondence, as measured using one of the following sequence comparison algorithms or by visual inspection. For clarity reasons, for example a sequence with at least 89.5% identity includes all sequences with identities higher than 89.5% identity, e.g. embodiments with at least 89.6%, at least 90%, at least 91%, at least 92%, at least 93%, at least 94%, at least 95%, at least 96%, at least 97%, at least 98%, at least 99%, or 100% amino acid identity. The percent identity exists in some embodiments over a region of at least 52 residues, in some embodiments over a region of at least 53 residues, in some embodiments over a region of at least 54 residues, in some embodiments over a region of at least 55 residues, in some embodiments over a region of at least 56 residues, in some embodiments over a region of at least 57 residues, and in some embodiments over a region of at least 58 residues.

The term "fused" means that the components are linked by peptide bonds, either directly or via peptide linkers.

The term "fusion protein" relates to a protein comprising at least a first protein joined genetically to at least a second protein. A fusion protein is created through joining of two or more genes that originally coded for separate proteins. Thus, a fusion protein may comprise a multimer of identical or different proteins which are expressed as a single, linear polypeptide As used herein, the term "linker" refers in its broadest meaning to a molecule that covalently joins at least two other molecules. In typical embodiments of the present invention, a "linker" is to be understood as a moiety that connects an Ig binding domain with at least one further Ig binding domain, i.e. a moiety linking two protein domains to each other to generate a multimer. In preferred embodiments, the "linker" is a peptide linker, i.e. the moiety linking the two protein domains is one single amino acid or a peptide comprising two or more amino acids.

The term "chromatography" refers to separation technologies which employ a mobile phase and a stationary phase to separate one type of molecules (e.g., immunoglobulins) from other molecules (e.g. contaminants) in the sample. The liquid mobile phase contains a mixture of molecules and transports these across or through a stationary phase (such as a solid matrix). Due to the differential interaction of the different molecules in the mobile phase with the stationary phase, molecules in the mobile phase can be separated.

The term "affinity chromatography" refers to a specific mode of chromatography in which a ligand coupled to a stationary phase interacts with a molecule (i.e. immunoglobulin) in the mobile phase (the sample) i.e. the ligand has a specific binding affinity for the molecule to be purified. As understood in the context of the invention, affinity chromatography involves the addition of a sample containing an immunoglobulin to a stationary phase which comprises a chromatography ligand, such as an Ig binding protein of the invention.

The terms "solid support" or "solid matrix" are used interchangeably for the stationary phase.

The terms "affinity matrix" or "affinity separation matrix" or "affinity chromatography matrix", as used interchangeably herein, refer to a matrix, e.g. a chromatographic matrix, onto which an affinity ligand e.g., an Ig binding protein of the invention is attached. The ligand (e.g., Ig binding protein) is capable of specific binding to a molecule of interest (e.g., an immunoglobulin as defined above) which is to be purified or removed from a mixture.

The term "affinity purification" as used herein refers to a method of purifying immunoglobulins as defined above from a liquid by binding immunoglobulins as defined above to an Ig binding protein that is immobilized to a matrix. Thereby, all other components of the mixture except immunoglobulins are removed. In a further step, immunoglobulins are eluted in purified form.

Embodiments of the Invention

The present invention will now be further described. In the following passages different embodiments of the invention are defined in more detail. Each embodiment defined below may be combined with any other embodiments unless clearly indicated to the contrary. In particular, any feature indicated as being preferred or advantageous may be combined with any other feature or features indicated as being preferred or advantageous.

In one embodiment, the Ig protein comprises one or more domains, wherein at least one domain comprises or essentially consists of or consists of an amino acid sequence of any of SEQ ID NO: 1-10, or of an amino acid sequence of any of SEQ ID NO: 1-7, or an amino acid with at least 89.5%, at least 90%, at least 91%, at least 92%, at least 93%, at least 94%, at least 95%, at least 96%, at least 97%, at least 98%, or at least 99% identity thereto. In some embodiments, the Ig protein comprises one or more domains, wherein at least one domain comprises or essentially consists of or consists of an amino acid sequence of any of SEQ ID NO: 1, 2, 3, 4, 5, 6, 7, 8, 9, or 10, or an amino acid with at least 95%, at least 96%, at least 97%, at least 98%, or at least 99% identity to any of SEQ ID NO: 1, 2, 3, 4, 5, 6, 7, 8, 9, or 10. The Ig binding domains of the invention are three-helix bundles of 58 amino acids with helix 1 from amino acid residues 7-19, helix 2 from amino acid residues 23-37, and helix 3 from amino acid residues 40-56.

The surprising advantage of the Ig binding proteins of the invention is the stability under extreme conditions such as under low pH or high pH (pH 13 and higher) without losing Ig binding properties. The Ig binding proteins as described herein demonstrate alkali stability for a prolonged period of time without impairing the Ig-binding properties. Further, they are stable at low pH without significantly losing Ig binding properties. The Ig binding proteins of the invention have less than 30% reduction in binding capacity following incubation in 0.5 M NaOH for at least 24 hours. This feature is important for chromatography approaches with cleaning procedures using alkaline solutions with high NaOH concentrations to remove contaminants on the matrix so for example that the matrix can be used several times. In addition to high caustic stability, Ig binding proteins show high coupling efficiencies. Further, an important step in affinity chromatography is the elution of the protein that is bound to the Ig binding protein of the invention. This step is usually done at low pH. The Ig binding proteins of the invention do not lose binding properties to Ig after this treatment.

Preferred Ig binding proteins. In some embodiments, an amino acid sequence of any one of SEQ ID NO: 1 (cs50), SEQ ID NO: 2 (cs52), SEQ ID NO: 3 (cs58), SEQ ID NO: 4 (cs59), SEQ ID NO: 5 (cs60), SEQ ID NO: 6 (cs51), SEQ ID NO: 7 (cs56), SEQ ID NO: 8 (cs54), SEQ ID NO: 9 (cs57), or SEQ ID NO: 10 (cs55) has 1 or 2 further substitutions. Some embodiments relate to amino acid sequences with at least 95% sequence identity to the amino acid sequence to any of SEQ ID NO: 1, 2, 3, 4, 5, 6, 7, 8, 9, or 10. Some embodiments relate to amino acid sequences with at least 98% sequence identity to the amino acid sequence to any of SEQ ID NO: 1, 2, 3, 4, 5, 6, 7, 8, 9, or 10.

In some embodiments, an Ig binding protein comprises one or more Ig binding domains, wherein at least one domain comprises or consists of an amino acid sequence of SEQ ID NOs: 1-7, or an amino acid sequence with at least 95% identity to any of SEQ ID NO: 1-7, wherein the Ig binding protein has an Ig-binding capacity at least 70% of the Ig binding capacity before the incubation under alkaline conditions, for example, as determined by the remaining Ig-binding capacity after at least 24 h incubation in 0.5 M NaOH.

Figures 1A, 1B:
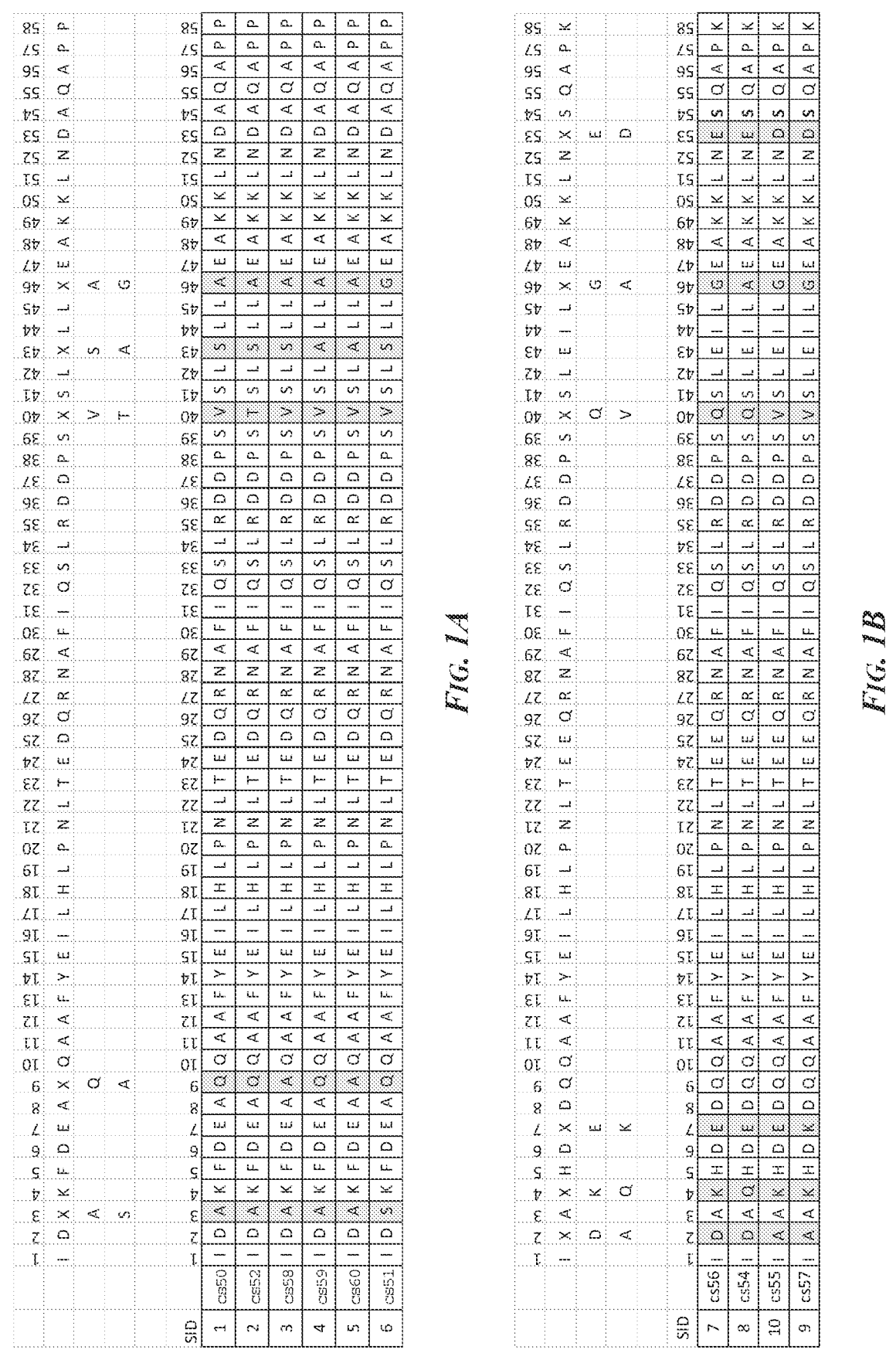

SEQ ID NO: 17. One embodiment covers an Ig binding protein that comprises one or more Ig binding domains that comprises or essentially consists or consists of the amino acid sequence of SEQ ID NO: 17 or at least 95% identical amino acid sequences thereto. The amino acid sequence of SEQ ID NO: 17 is shown in FIG. 1A and here:

IDX$_3$KFDEAX$_9$QAAFYEILHLPNLTEEQRNAFIQSLRDDPS X$_{40}$SL
X$_{43}$LLX$_{46}$EAKKLNDAQAPP wherein the amino acid at position 3 (X$_3$) is selected from A or S, the amino acid at position 9 (X$_9$) is selected from Q or A, the amino acid at position 40 (X$_{40}$) is selected from T or V, the amino acid at position 43 (X$_{43}$) is selected from S or A, and the amino acid at position 46 (X$_{46}$) is selected from G or A.

Selected examples for amino acid sequences of SEQ ID NO: 17 are SEQ ID NOs: 1-6, as shown in FIG. 1A. In some embodiments, the Ig binding protein is comprising one or more domains of an amino acid sequence of SEQ ID NO: 1, or of a sequence with at least 89.5% sequence identity thereto. For example, amino acid sequences with at least 89.5% identity, preferably at least 95% identity, to SEQ ID NO: 1 include but are not limited to SEQ ID NO: 2 (cs52; 98.3% identity to SEQ ID NO: 1), SEQ ID NOs: 3 (cs58; 98.3% identity to SEQ ID NO: 1), SEQ ID NO: 4 (cs59; 98.3% identity to SEQ ID NO: 1), SEQ ID NO: 5 (cs60; 96.6% identity to SEQ ID NO: 1), and SEQ ID NO: 6 (cs51; 96.6% identity to SEQ ID NO: 1). See Table 1 for amino acid identities of exemplary amino acid sequences of SEQ ID NO: 17.

TABLE 1

| | Amino acid identities of SEQ ID NOs: 1-6 | | | | | | |
| | | SEQ ID | | | | | |
| SEQ ID | variant | 1 cs50 | 2 cs52 | 3 cs58 | 4 cs59 | 5 cs60 | 6 cs51 |
|---|---|---|---|---|---|---|---|
| 1 | cs50 | 100 | 98.3 | 98.3 | 98.3 | 96.6 | 96.6 |
| 2 | cs52 | 98.3 | 100 | 96.6 | 96.6 | 94.8 | 94.8 |
| 3 | cs58 | 98.3 | 96.6 | 100 | 96.6 | 98.3 | 94.8 |
| 4 | cs59 | 98.3 | 96.6 | 96.6 | 100 | 98.3 | 94.8 |
| 5 | cs60 | 96.6 | 94.8 | 98.3 | 98.3 | 100 | 93.1 |
| 6 | cs51 | 96.6 | 94.8 | 94.8 | 94.8 | 93.1 | 100 |

SEQ ID NO: 18. One embodiment covers an Ig binding protein that comprises one or more Ig binding domains that comprises or essentially consists or consists of the amino acid sequence of SEQ ID NO: 18 or at least 89.5% identical amino acid sequences thereto. The amino acid sequence of SEQ ID NO: 18 is shown in FIG. 1B and here:

IX$_2$AX$_4$HDX$_7$DQQAAFYEILHLPNLTEEQRNAFIQSLRDDPSX$_{40}$SLEILX$_{46}$
EAKKLNX$_{53}$SQAPK wherein the amino acid at position 2 (X$_2$) is selected from A or D, the amino acid at position 4 (X$_4$) is selected from K or Q, the amino acid at position 7 (X$_7$) is selected from K or E, the amino acid at position 40 (X$_{40}$) is selected from Q or V, the amino acid at position 46 (X$_{46}$) is selected from G or A, the amino acid at position 53 (X$_{53}$) is selected from D or E.

Selected examples for amino acid sequences of SEQ ID NO: 18 are SEQ ID NOs: 7-10, as shown in FIG. 1B. In some embodiments, the Ig binding protein is comprising one or more domains of an amino acid sequence of SEQ ID NO: 7 or of an amino acid sequence with at least 92% identity. For example, amino acid sequences with at least 89.5% identity to SEQ ID NO: 7 include but are not limited to SEQ ID NO: 8 (cs54; 96.6% identity to SEQ ID NO: 7), SEQ ID NO: 10 (cs55; 94.8% identity to SEQ ID NO: 7), and SEQ ID NOs: 9 (cs57; 93.1% identity to SEQ ID NO: 7). See Table 2 for amino acid identities for examples for amino acid sequences of SEQ ID NO: 18.

TABLE 2

| | Amino acid identities of SEQ ID NOs: 7-10 | | | | |
| | | SEQ ID | | | |
| SEQ ID | variant | 7 cs56 | 8 cs54 | 9 cs57 | 10 cs55 |
|---|---|---|---|---|---|
| 7 | cs56 | 100 | 96.6 | 93.1 | 94.8 |
| 8 | cs54 | 96.6 | 100 | 89.7 | 91.4 |
| 9 | cs57 | 93.1 | 89.7 | 100 | 98.3 |
| 10 | cs55 | 94.8 | 91.4 | 98.3 | 100 |

In some embodiments, the Ig binding protein is comprising one or more domains of an amino acid sequence as set forth in SEQ ID NOs: 1-8, or a sequence at least 92% identical to any of SEQ ID NOs: 1-8.

In some embodiments, the Ig binding protein is comprising one or more domains of an amino acid sequence as set forth in SEQ ID NO: 8 (cs54), or a sequence at least 92% identical thereto. In other embodiments, the Ig binding protein is comprising one or more domains of an amino acid sequence as set forth in SEQ ID NO: 10 (cs55), or an amino acid sequence at least 94% identical thereto, preferably at least 95% identical thereto. In some embodiments, the Ig binding protein is comprising one or more domains of an amino acid sequence as set forth in SEQ ID NOs: 1-10, preferably SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 10, or a sequence at least 95% identical to any of SEQ ID NOs: 1-10, preferably to any of SEQ ID NO: 1, 2, 3, 4, 5, 6, 7, 8, or 10. In other embodiments, the Ig binding protein is comprising one or more domains of an amino acid sequence as set forth in SEQ ID NO: 9 (cs57), or an amino acid sequence at least 95% identical, preferably at least 98% identical, thereto.

In other embodiments, the Ig binding protein is comprising one or more domains of an amino acid sequence as set forth in SEQ ID NOs: 8, 9, 10, or a sequence at least 89.5% identical to any of SEQ ID NOs: 8, 9, 10, provided that the amino acid corresponding to position 54 is a serine.

Affinity to Immunoglobulin. All Ig binding proteins of the invention bind to Immunoglobulin with a dissociation constant K$_D$ preferably below 500 nM, or below 100 nM, even more preferably 10 nM or less. Methods for determining binding affinities of Ig binding proteins or domains, i.e. for determining the dissociation constant K$_D$, are known to a person of ordinary skill in the art and can be selected for instance from the following methods known in the art: Surface Plasmon Resonance (SPR) based technology, kinetic exclusion analysis (KinExA assay), Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Some of the methods are described further in the Examples. Typically, the dissociation constant K$_D$ is determined at 20° C., 25° C., or 30° C. If not specifically indicated otherwise, the K$_D$ values recited herein are determined at 22° C.+/−3° C. by surface plasmon resonance. In one embodiment, the Ig binding protein has a dissociation constant K$_D$ to human $IgG_1$ in the range between 0.1 nM and 100 nM, preferably between 0.1 nM and 50 nM (see Example 6, Table 3).

High alkaline stability of Ig binding proteins. The Ig binding proteins of the invention provide surprisingly particularly good alkaline stability of the Ig binding protein, as shown in the Examples and in the Figures. The alkaline stability of the Ig binding protein is determined by comparing the loss in Ig binding activity. In some embodiments, the alkaline liquid comprises 0.1-1.0 M NaOH or KOH, preferably 0.25-0.5 M NaOH or KOH. Due to the high alkaline stability of the Ig binding proteins of the invention, an alkaline liquid with pH higher than 13 can be used for cleaning affinity matrices with immobilized Ig binding protein of the invention. In some embodiments, the alkaline stability of the Ig binding protein is determined by comparing the loss in Ig binding activity after at least 24 h incubation in 0.5 M NaOH (see FIG. 4 and Examples).

Multimers. In one embodiment, the Ig binding protein comprises 1, 2, 3, 4, 5, 6, 7, or 8, preferably 2, 3, 4, 5, or 6, Ig binding domains linked to each other, i.e. the Ig binding protein can be, for example, a monomer, a dimer, a trimer, a tetramer, a pentamer, or a hexamer. A multimer may comprise two, three, four, or even more binding domains. Multimers of the invention are fusion proteins generated artificially, generally by recombinant DNA technology well-known to a skilled person.

In some embodiments, the multimer is a homo-multimer, e.g. the amino acid sequences of all Ig binding domains of the Ig binding protein are identical.

A multimer may comprise two or more Ig binding domains, wherein said Ig binding domains preferably comprise or essentially consist of a sequence as described above. Examples for dimers are provided in SEQ ID NO: 11 (cs58 dimer), SEQ ID NO: 12 (cs59 dimer), SEQ ID NO: 13 (cs60 dimer), and SEQ ID NO: 14 (cs50 dimer). Examples for pentamers are provided in SEQ ID NO: 15 (cs50 pentamer) and SEQ ID NO: 16 (cs59 pentamer).

In some embodiments, the multimer is a hetero-multimer, e.g. at least one Ig binding domain has a different amino acid sequence than the other Ig binding domains within the Ig-binding protein.

Linker. In some embodiments of the one embodiment, the one or more Ig binding domains are directly linked to each other. In other embodiments, the one or more Ig binding domains are linked to each other with one or more linkers. Preferred in these typical embodiments are peptide linkers. This means that the peptide linker is an amino acid sequence that connects a first Ig binding domain with a second Ig binding domain. The peptide linker is connected to the first Ig binding domain and to the second Ig binding domain by a peptide bond between the C-terminal and N-terminal ends of the domains, thereby generating a single, linear polypeptide chain. The length and composition of a linker may vary between at least one and up to about 30 amino acids. More specifically, a peptide linker has a length of between 1 and 30 amino acids; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acids. It is preferred that the amino acid sequence of the peptide linker is stable against caustic conditions and proteases. Linkers should not destabilize the conformation of the domains in the Ig binding protein. Well-known are linkers that comprise or consist of small amino acids such as glycine and serine. The linkers can be glycine-rich (e.g., more than 50% of the residues in the linker can be glycine residues). Also preferred are linkers that comprise further amino acids. Other embodiments of the invention comprise linkers consisting of alanine, proline, and serine. Other linkers for the fusion of proteins are known in the art and can be used. In some embodiments, the multimer of Ig binding proteins comprises one or more linkers connecting the Ig binding domains wherein the linkers are identical or different.

Affinity separation matrix. In another embodiment the present invention is directed to an affinity separation matrix, comprising an Ig binding protein of the previous embodiments.

In preferred embodiments, the affinity separation matrix is a solid support. The affinity separation matrix comprises at least one Ig binding protein as described above.

An affinity matrix is useful for separation of immunoglobulins and should retain the Ig binding property even after highly alkaline conditions as applied during cleaning processes. Such cleaning of matrices is essential for long-term repeated use of matrices.

Solid support matrices for affinity chromatography are known in the art and include for example but are not limited to, agarose and stabilized derivatives of agarose (e.g. PRAE-STO® PURE brand chromatography medium (Ecolab Purolite Resins. St. Paul, Minnesota, United States of America), PRAESTO® Jetted ASO brand chromatography medium (Ecolab Purolite Resins, St. Paul, Minnesota, United States of America), MABSELECT® brand chromatography medium (Cytiva Bioprocess R&D AB. Uppsala, Sweden), PRISMA® brand chromatography medium (Cytiva Bioprocess R&D AB Uppsala, Sweden), SEPHAROSE® 6B® brand chromatography medium (Cytiva Bioprocess R&D AB, Uppsala, Sweden), CAPTIVA® brand chromatography medium (Repligen Corporation, Waltham, Massachusetts, United States of America), rPROTEIN A SEPHAROSE® Fast Flow brand chromatography medium (Cytiva Bioprocess R&D AB, Uppsala, Sweden), and other), cellulose or derivatives of cellulose, controlled pore glass (e.g., PROSEP® vA brand chromatography resin; Merck KGaA, Darmstadt, Germany), monolith (e.g., CIM® monoliths brand chromatography medium, Sartorius BIA Separations, Ajdovščina, Slovenia), silica, zirconium oxide (e.g., CM Zirconia or CPG®), titanium oxide, or synthetic polymers (e.g. polystyrene such as POROS™ 50A or POROS™ MABCAPTURE™ A brand affinity chromatography resin (Thermo Fisher Scientific, Waltham, Massachusetts, United States of America), polyvinylether, polyvinyl alcohol, monodisperse polyacrylate resin (e.g. UNIMAB™ brand affinity chromatography resin, Suzhou NanoMicro Technology Co Ltd., Suzhou Industrial Park, China; UNIMAB™ Pro brand affinity chromatography resin, Suzhou NanoMicro Technology Co Ltd., Suzhou Industrial Park, China), polyhydroxyalkyl acrylates, polyhydroxyalkyl methacrylates, polyacrylamides, polymethacrylamides, etc.) and hydrogels of various compositions. In certain embodiments the support comprises a polyhydroxy polymer, such as a polysaccharide. Examples of polysaccharides suitable for supports include but are not limited to agar, agarose, dextran, starch, cellulose, pullulan, etc., and stabilized variants of these.

The formats for solid support matrices can be of any suitable well-known kind. Such solid support matrix for coupling the Ig binding protein as described herein might comprise for example, one of the following: columns, capillaries, particles, membranes, filters, monoliths, fibers, pads, gels, slides, plates, cassettes, or any other format commonly used in chromatography and known to someone skilled in the art.

In one embodiment, the matrix is comprised of substantially spherical particles, also known as beads, for example Sepharose or Agarose beads or monodisperse polyacrylate beads. Suitable particle sizes may be in the diameter range of 5-500 μm, such as 10-100 μm, such as 20-80 μm, such as 40-70 μm. Matrices in particle form can be used as a packed bed or in a suspended form including expanded beds.

In an alternative embodiment, the solid support matrix is a membrane, for example a hydrogel membrane. In some embodiments, the affinity purification involves a membrane as matrix to which the Ig binding protein of the one embodiment is covalently bound. The solid support can also be in the form of a membrane in a cartridge.

In some embodiments, the affinity purification involves a chromatography column containing a solid support matrix to which the Ig binding protein of the one embodiment is covalently bound.

Immobilization to a solid support. In embodiments of the invention, the Ig binding protein is conjugated to a solid support. In some embodiments of the invention, the Ig binding protein may comprise additional amino acid residues at the N- and/or C-terminal end. The Ig binding protein of the invention may be attached to a suitable solid support matrix via conventional coupling techniques. Methods for immobilization of protein ligands to solid supports are well-known in this field and easily performed by the skilled person in this field using standard techniques and equipment. In some embodiments, the coupling may be a multi-point coupling, for example via several lysines, or a single point coupling, for example via cysteine.

In some embodiments, the alkaline stable Ig binding protein comprises an attachment site for covalent attachment to a solid phase (matrix). Site-specific attachment sites comprise natural amino acids, such as cysteine or lysine, which enable specific chemical reactions with a reactive group of the solid phase or a linker between the solid phase and the protein.

In some embodiments, the attachment site may be directly at the C- or N-terminal end of the Ig binding protein. In some embodiments, a single cysteine is located at the C-terminal end for site-specific immobilization of the Ig binding protein. An advantage of having a C-terminal cysteine is that coupling of the Ig binding protein can be achieved through reaction of the cysteine thiol with an electrophilic group on a support resulting in a thioether bridge coupling. This provides excellent mobility of the coupled protein which provides increased binding capacity.

In other embodiments, there may be a linker between the N- or C-terminus and the attachment site. In some embodiments of the invention, the Ig binding protein may comprise a N- or C-terminal amino acid sequence of 3-20 amino acids, preferably of 4-10 amino acids, with a terminal cysteine. Amino acids for a terminal attachment site may be selected from the group of proline, glycine, alanine, and serine, with a single cysteine at the C-terminal end for coupling.

In some embodiments of the invention, the Ig binding protein may also comprise additional amino acid residues at the N- and/or C-terminal end, such as for example a leader sequence at the N-terminal end and/or a coupling sequence with or without a tag at the N- or C-terminal end.

Use of the Ig binding protein. In a one embodiment the present invention is directed to the use of the Ig binding protein of the one embodiment or an affinity matrix of the one embodiment for affinity purification of immunoglobulins or variants thereof, i.e. the Ig binding protein of the invention is used for affinity chromatography. In some embodiments, the Ig binding protein of the invention is immobilized onto a solid support as described in the one embodiment of the invention.

Method of affinity purification of immunoglobulins. In one embodiment the present invention is directed to a method of affinity purification of immunoglobulins, the method comprising the following steps:
(a) providing a liquid that contains an Ig such as $IgG_1$, $IgG_2$, $IgG_4$, IgM, IgA, Ig fragments, Fc fragments, or Fab fragments (including fusion proteins and conjugates, as defined above);
(b) providing an affinity separation matrix comprising an immobilized Ig binding protein as described above immobilized to said affinity separation matrix;
(c) contacting said liquid with said affinity separation matrix, under conditions that permit binding of the at least one Ig binding protein as described above to an Ig; and
(d) eluting said Ig from said matrix, thereby obtaining an eluate containing said Ig.

In some embodiments, the method of affinity purification may further comprise one or more washing steps carried out between steps (c) and (d) under conditions sufficient to remove from the affinity separation matrix some or all molecules that are non-specifically bound thereto. Non-specifically bound means any binding that does not involve an interaction between the at least one Ig binding protein and an Ig.

Affinity separation matrices suitable for the disclosed uses and methods are those matrices according to the embodiments described above and as known to someone skilled in the art.

In some embodiments, the elution of the immunoglobulin from Ig binding protein in step (d) is effected through a change in pH and/or a change in salt concentration. In general, suitable conditions for performing the method of affinity purification are well known to someone skilled in the art. In some embodiments, the disclosed uses or methods of affinity purification comprising the disclosed Ig binding proteins may provide elution of at least about 90%, at least about 95%, at least about 96%, at least about 97%, at least about 98%, at least about 99%, or 100% of Ig containing proteins at a pH of greater than or equal to 3.5 (e.g., about 3.8, about 4.0, or about 4.5). Due to the high stability of the Ig binding proteins of the invention, solutions with greater than or equal to pH 3.5 can be used for the elution of Ig proteins (see Example 6).

In some embodiments, a further step (f) for efficient cleaning of the affinity matrix is added, preferably by using an alkaline liquid, for example, with pH of 13-14. In certain embodiments, the cleaning liquid comprises 0.1-1.0 M NaOH or KOH, preferably 0.25-0.5 M NaOH or KOH. Due to the high alkaline stability of the Ig binding proteins of the invention, such strong alkaline solution can be used for cleaning purposes.

Figure 4:
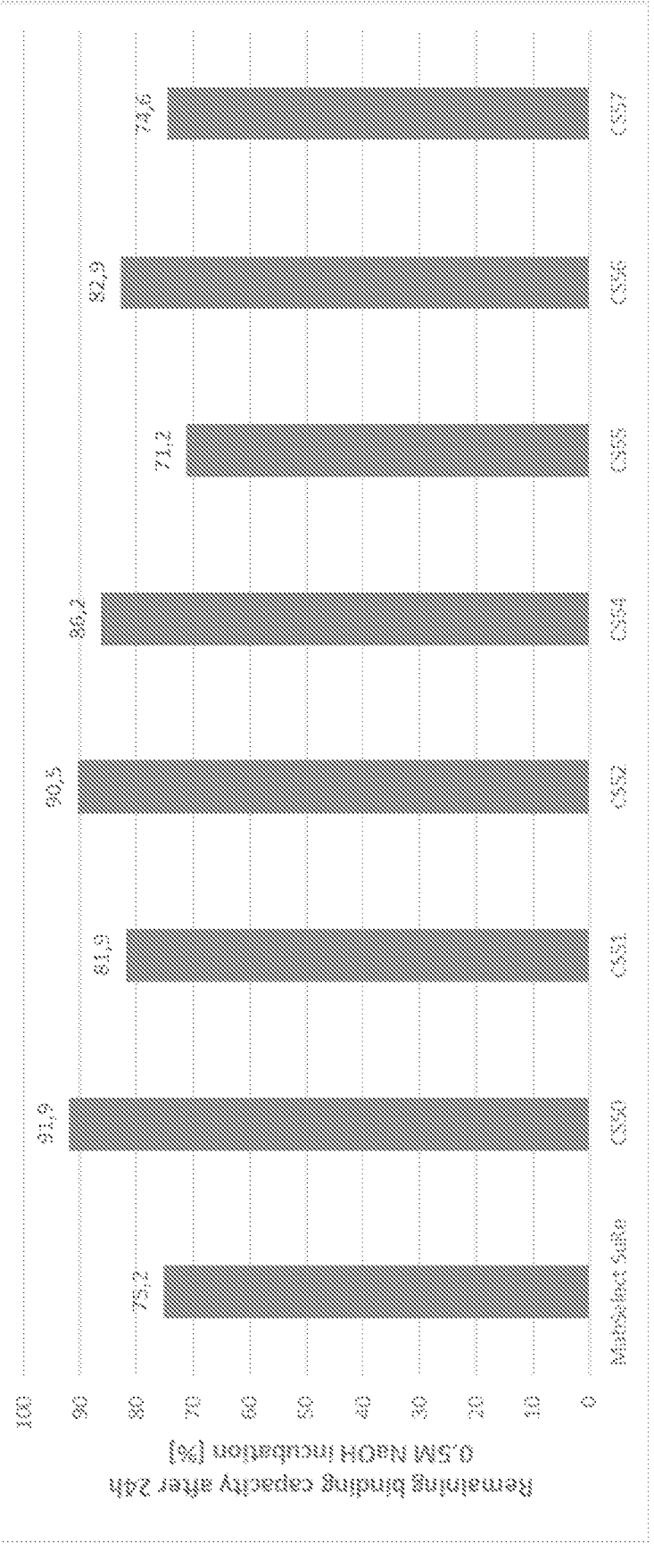
FIG. 4. Caustic stability of Ig binding proteins of the invention.

In some embodiments, the Ig-binding capacity of the Ig binding protein is at least 70%, at least about 80%, at least about 90%, or 100% of the Ig binding capacity before the incubation under alkaline conditions, for example, as determined by the remaining Ig-binding capacity after at least 24 h incubation in 0.5 M NaOH (see FIG. 4 and Examples).

In some embodiments, the affinity matrix can be re-used at least 10 times, at least 20 times, at least 30 times, at least 40 times, at least 50 times, at least 60 times, at least 70 times, at least 80 times, at least 90 times, or at least 100 times, due to a repetition of steps (a) to (e), optionally (a) to (f) can be repeated at least 10 times, at least 20 times, at least 30 times, at least 40 times, at least 50 times, at least 60 times, at least 70 times, at least 80 times, at least 90 times, or at least 100 times.

Nucleic acid molecule. In one embodiment, the present invention is directed to a nucleic acid molecule, preferably an isolated nucleic acid molecule, encoding an Ig binding protein as disclosed above. In one embodiment, the present invention is directed to a vector comprising the nucleic acid molecule. A vector means any molecule or entity (e.g., nucleic acid, plasmid, bacteriophage or virus) that can be used to transfer protein coding information into a host cell. In one embodiment, the vector is an expression vector.

In one embodiment, the present invention is directed to an expression system which comprises a nucleic acid or a vector as disclosed above, for example a prokaryotic host cell, for example E. coli, or a eukaryotic host, for example yeast Saccharomyces cerevisiae or Pichia pastoris or mammalian cells such as CHO cells.

Method for the production of an Ig binding protein. In one embodiment the present invention is directed to a method for the production of a Ig binding protein of the invention, comprising the step(s): (a) culturing the host cell of the one embodiment under suitable conditions for the expression of the binding protein in order to obtain said Ig binding protein; and (b) optionally isolating said Ig binding protein. Suitable conditions for culturing a prokaryotic or eukaryotic host are well-known to the person skilled in the art.

Ig binding molecules of the invention may be prepared by any of the many conventional and well-known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

One embodiment of the present invention is directed to a method for the preparation of a Ig binding protein according to the invention as detailed above, said method comprising the following steps: (a) preparing a nucleic acid encoding an Ig binding protein as defined above; (b) introducing said nucleic acid into an expression vector; (c) introducing said expression vector into a host cell; (d) cultivating the host cell; (e) subjecting the host cell to culturing conditions under which an Ig binding protein is expressed, thereby (e) producing an Ig binding protein as described above; optionally (f) isolating the protein produced in step (e); and (g) optionally conjugating the protein to solid matrices as described above.

In a further embodiment of the present invention the production of the Ig binding protein is performed by cell-free in vitro transcription/translation.

EXAMPLES

The following Examples are provided for further illustration of the invention. The invention, however, is not limited thereto, and the following Examples merely show the practicability of the invention on the basis of the above description.

Example 1. Generation of Ig Binding Proteins of the Invention

Artificial Ig binding ligands were initially generated by a shuffling process of naturally occurring Protein A domains and Protein A domain variants (e.g. Z domain). In more detail, the shuffling process as understood herein is an assembly process resulting in artificial amino acid sequences starting from a set of non-identical known amino acid sequences. The shuffling process comprised the following steps: a) providing sequences of five naturally occurring Protein A domains E, B, D, A, and C, and Protein A variant domain Z; b) alignment of said sequences; c) statistical fragmentation in silico to identify subsequences that were recombined, and then d) assembly of new, artificial sequences of the various fragments to produce a mosaic product, i.e. a novel amino acid sequence. The fragments generated in step c) were of any length, e.g. if the fragmented parent sequence had a length of n, the fragments was of length 1 to n−1.

The relative positions of the amino acids in the mosaic products were maintained with respect to the starting amino acid sequences. The overall amino acid sequence of the artificial, shuffled Ig binding proteins is artificial in that it is not more than 85% identical to the overall amino acid sequence of any of the naturally occurring Protein A domains or domain Z. After the initial artificial Ig binding proteins was generated, the protein was further modified by site-specific randomization of the amino acid sequence to further modify functional properties. The further modifications were introduced by site-saturation mutagenesis of individual amino acid residues. For example, the amino acid sequence of an alkaline stable Ig binding protein cs26 (SEQ ID NO: 19) was generated by this approach.

Variants cs50, cs52, cs58, cs59, cs60, cs51, cs56, cs54, cs55, and cs57 were generated by synthetic gene fragments (Twist Bioscience/Thermo Fisher Scientific). The gene fragments corresponded to a purified PCR product and were cloned into a derivate of a pET28a vector. Ligation products were transformed into E. coli XL2-blue cells (Stratagene) via electroporation. Single colonies were screened by PCR to identify constructs containing inserts of the right size. DNA sequencing was used to verify the correct sequences. All variants of the invention have less than 80% identity to for example naturally occurring Protein A domain C, Protein A domain B, or to domain Z.

Example 2. Expression of Ig Binding Proteins

BL21 (DE3) competent cells were transformed with an expression plasmid encoding Ig binding proteins. Cells were spread onto selective agar plates (Kanamycin) and incubated overnight at 37° C. Precultures were inoculated from single colony in 50 ml 2×YT medium supplemented with 50 μg/ml kanamycin and cultured for 17 hours at 37° C. at 200 rpm in a conventional orbital shaker in 500 mL Erlenmeyer flasks. The $OD_{600}$ readout should be in the range of 4-6. Main cultures were inoculated from previous overnight culture with an adjusted start-$OD_{600}$ of 0.3 in 300 ml superrich medium (modified H15 medium consisting of 2% glucose, 5% yeast extract, 0.89% glycerol, 0.76% lactose, 250 mM MOPS, 202 mM TRIS, 10 mM $MgSO_4$, pH 7.4, antifoam SE15) that was supplemented with 50 μg/ml Kanamycin and trace elements (see Studier 2005) in 1 L thick-walled Erlenmeyer flasks. Cultures were transferred to a resonant acoustic mixer ($RAM_{bio}$) and incubated at 37° C. with 20×g. Aeration was facilitated by Oxy-Pump stoppers. Recombinant protein expression was induced by metabolizing glucose and subsequently allowing lactose to enter the cells. Cells were grown overnight for approx. 18 hours to reach a final $OD_{600}$ of about 30-45. Before the harvest, the $OD_{600}$ was measured, samples adjusted to 0.6/$OD_{600}$ were withdrawn, pelleted and frozen at −20° C. To collect biomass cells were centrifuged at 12000×g for 15 min at 20° C. Pellets were weighed (wet weight). Cells were stored at −20° C. before processing.

Example 3: SDS-PAGE Analysis of Expression and Solubility of Ig Binding Proteins Samples were resuspended in 90 µl extraction buffer (PBS supplemented with 0.2 mg/ml Lysozyme, 0.5× BugBuster, 6 mM MgSO$_4$, 6 mM MgCl$_2$, 15 U/mL Benzonase) and solubilized by agitation in a thermomixer at 850 rpm, rt for 15 min with a subsequent incubation at −80° C. for 15 min. After thawing, soluble proteins were separated from insoluble proteins by centrifugation (16000×g, 2 min, rt). Supernatant was withdrawn (soluble fraction) and the pellet (insoluble fraction) was resuspended in equivalent amount of urea buffer (8 M urea, 0.2 M Tris, 20 mM EDTA, pH 7.0). 35 µl were taken both from the soluble and insoluble fraction, and 10 µl 5× sample buffer as well as 5 µl 0.5 M DTT were added. Samples were boiled at 95° C. for 5 min. Finally, 5 µl of those samples were applied to NuPage Novex 4-12% Bis-Tris SDS gels which were run in accordance to the manufacturer's recommendations and stained with Coomassie. High level expression of all Ig binding proteins was found under optimized conditions within the chosen period of time (data not shown). All expressed Ig binding proteins were soluble to more than 95% according to SDS-PAGE.

Example 4: Purification of Ig Binding Proteins

Ig binding proteins were expressed in the soluble fraction of *E. coli*. The cells were resuspended in cell disruption buffer and lysed by an ultrasonic cell disruption system (Sonopuls HD 2200, Bandelin). Purification step was performed with IEC Sepharose SP-HP (GE Healthcare) using an ÄKTAvant system (Ge Healthcare) according to the manufacturer's instructions using citric acid buffer at pH 3.0 (20 mM Citric acid, 1 mM EDTA, pH 3.0). Pure protein fractions were eluted by increasing sodium chloride concentration to 1 M with a linear gradient in 10 column volumes.

Example 5. The Ig Binding Proteins Bind to IgG with High Affinities (as Determined with Surface Plasmon Resonance Experiments)

A CM5 sensor chip (GE Healthcare) was equilibrated with SPR running buffer. Surface-exposed carboxylic groups were activated by passing a mixture of EDC and NHS to yield reactive ester groups. 700-1500 RU on-ligand were immobilized on a flow cell, off-ligand was immobilized on another flow cell. Injection of ethanolamine after ligand immobilization removes non-covalently bound Ig binding protein. Upon ligand binding, protein analyte was accumulated on the surface increasing the refractive index. This change in the refractive index was measured in real time and plotted as response or resonance units (RU) versus time. The analytes were applied to the chip in serial dilutions with a suitable flow rate (µl/min). After each run, the chip surface was regenerated with regeneration buffer and equilibrated with running buffer. The control samples were applied to the matrix. Regeneration and re-equilibration were performed as previously mentioned. Binding studies were carried out by the use of the Biacore® 3000 (GE Healthcare) at 25° C.; data evaluation was operated via the BIAevaluation 3.0 software, provided by the manufacturer, by the use of the Langmuir 1:1 model (RI=0). Evaluated dissociation constants (K$_D$) were standardized against off-target and K$_D$ values of different artificial Ig binding proteins for Cetuximab (IgG$_1$) are shown in Table 3A and for Cetuximab (IgG$_1$), Natalizumab (IgG$_4$), and Panitumab (IgG$_2$) in Table 3B.

Table 3. The Ig Binding Proteins Bind to IgG with High Affinities

TABLE 3A

| SEQ ID NO: | Affilin- | Alias | Kd [nM] IgG$_1$ (Cetuximab) |
|---|---|---|---|
| | | domain C | 5.7 |
| 1 | 194928 | cs50 | 5.08 |
| 6 | 194929 | cs51 | 6.05 |
| 2 | 194930 | cs52 | 7.41 |
| 8 | 194932 | cs54 | 36.4 |
| 10 | 194933 | cs55 | 9.2 |
| 7 | 194934 | cs56 | 14.8 |
| 9 | 194935 | cs57 | 3.9 |

*K$_D$ values of Ig binding proteins for IgG$_1$*

TABLE 3B

K$_D$ values of Ig binding proteins for IgG$_1$ (Cetuximab), IgG$_4$ (Natalizumab) and IgG$_2$(Panitumab)

| SEQ ID NO: | Affilin- | Alias | Kd [nM] IgG$_1$ | Kd [nM] IgG$_4$ | Kd [nM] IgG$_2$ |
|---|---|---|---|---|---|
| 1 | 194928 | cs50 | 5.1 | 2.6 | 25.1 |
| 14 | 203930 | cs50 dimer | 6.5 | 3.5 | 25.7 |
| 15 | 203931 | cs50 pentamer | 1.1 | 1.2 | 15 |
| 11 | 203927 | cs58 dimer | 21.2 | 6.1 | n.d. |
| 12 | 203928 | cs59 dimer | 4.9 | 0.5 | 18.1 |
| 16 | 203932 | cs59 pentamer | 0.7 | 0.9 | 13.8 |
| 13 | 203929 | cs60 dimer | 2.4 | 8.8 | n.d. |

Figure 3A:
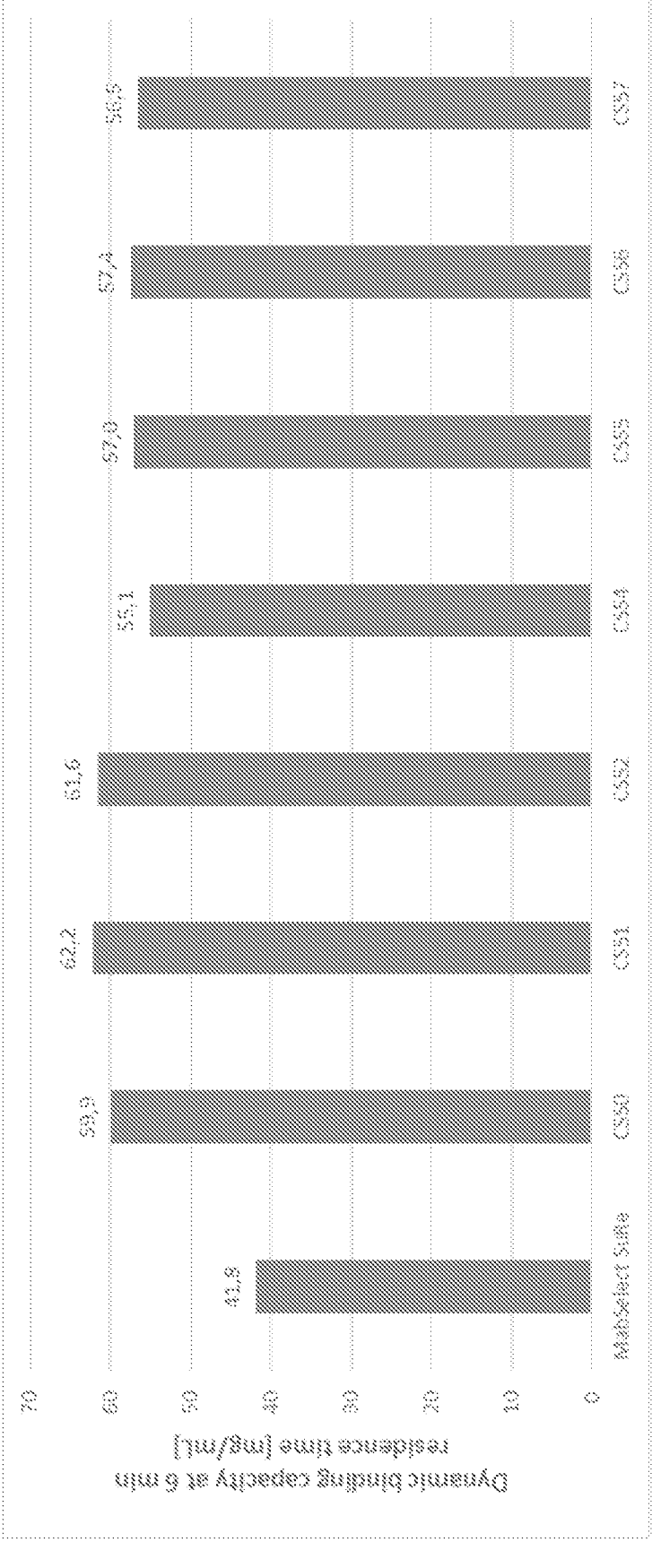
FIG. 3A. The dynamic binding capacity (DBC; mg/ml) is shown for Ig binding proteins, compared to commercially available protein resin MABSELECT SURE® brand chromatography medium (Cytiva Bioprocess R&D AB. Uppsala, Sweden) FIG. 3B. Improved dynamic binding capacity (DBC; mg/ml) of Ig binding proteins, compared to MAB-SELECT SURE® brand chromatography medium (Cytiva Bioprocess R&D AB, Uppsala, Sweden).
Figure 3B:
FIG. 3. Dynamic binding capacity of Ig binding proteins of the invention.

Example 6. Ig Binding Proteins Coupled to
Agarose-Based Chromatography Beads
PRAESTO® Pure85 Brand Chromatography
Medium (Ecolab Purolite Resins, St. Paul,
Minnesota, United States of America)—Coupling
Efficiencies, DBC10%, Elution Purified Ig binding proteins were coupled to agarose-based chromatography beads PRAESTO® Pure 85 brand chromatography medium (Ecolab Purolite Resins, St. Paul, Minnesota, United States of America), Cat. No. PR01265-164) according to the manufacturer's instructions (coupling conditions: pH 9.5, 3 hours, 35° C., 4.1 M NaSO$_4$, blocking overnight with ethanolamine). See FIG. 2 for coupling efficiencies. Coupled Resin and commercial MABSE-LECT® brand chromatography medium (Cytiva Bioprocess R&D AB, Uppsala, Sweden; Cat. No. 29049104, GE-Healthcare) was packed into super compact 5/50 column (Gotec GmbH). Polyclonal human IgG GAMMANORM® brand human normal immunoglobulin. Octapharma Bio-pharmaceuticals GmbH, Frankfurt, Germany) was used as IgG sample (conc. 2.2 mg/ml). Polyclonal hIgG sample was applied in saturated amounts to the matrix comprising immobilized Ig binding protein. See FIGS. 3A and 3B for dynamic binding capacities (DBC, mg/ml). Comparable results were obtained with 20 mg/ml cs59 (dimer) or cs60 (dimer) coupled to PRAESTO® 85 epoxy resin brand chromatography medium (Ecolab Purolite Resins, St. Paul, Minnesota, United States of America; coupling conditions: pH 9.5, 3 hours, 35° C., 350 mg/ml resin Na$_2$SO$_4$).

The matrix was washed with 50 mM acetic acid buffer, pH 3.5 and then with 0.1 M phosphoric acid to elute hIgG that was bound to the immobilized Ig binding protein. For all Ig binding proteins tested, more than 97% of the antibody was eluted (100%, cs55, cs56, cs57; 99.5% for cs54; 98.3% for cs52, 97.4% for cs51, and 97.3% for cs50). Alternatively, the matrix was washed with 100 mM acetic acid buffer, pH 3.7 and then with 0.1 M phosphoric acid to elute hIgG that was bound to the immobilized Ig binding protein. More than 98% of the antibody was eluted from a matrix with immobilized cs60 (dimer).

Example 7. Alkaline Stability of Ig Binding
Proteins Coupled to an Epoxy-Activated Matrix Columns were incubated with 0.5 M NaOH for 0 h and 24 h at room temperature (22° C.+/−3° C.). The Ig binding activity of the immobilized proteins was analyzed before and after incubation with 0.5 M NaOH. Results are shown in FIG. 4. Further, the caustic stability was analyzed for some Ig binding proteins after 48 h at 0.5 M NaOH. Even after 2 d of incubation in strong alkaline solution, the remaining binding capacity was 79% for cs50, 75.2% for cs52, and 61.4% for cs56. Compared to MABSELECT® Sure brand chromatography medium (Cytiva Bioprocess R&D AB, Uppsala, Sweden), the binding capacity was improved at least 38.9% (cs56), 70.1% (cs52), and 78.7% (cs50).

PRAESTO™ 85 brand epoxy resin (Ecolab Purolite Resins, St. Paul, Minnesota, United States of America) with immobilized 20 mg/ml cs59 (dimer) or cs60 (dimer) was incubated with 0.5 M NaOH for 24 h and 50 h at room temperature (22° C.+/−3° C.). Even after more than 2 days in strong alkaline solution, cs59 (dimer) and cs60 (dimer) showed 95.3% and 98.6%, respectively, remaining binding capacity for Ig. The remaining IgG binding capacity of cs59 and cs60 after alkaline treatment for 50 h is improved compared to caustic stable protein of SEQ ID NO: 19 (88% remaining binding capacity for Ig).

The invention claimed is:

1. An Ig binding protein comprising one or more Ig binding domains, wherein the one or more Ig binding domains comprise or consist of an amino acid of any one of SEQ ID NOs: 1-5.

2. The Ig binding protein according to claim 1, wherein the protein comprises 2, 3, 4, 5, 6, 7, or 8 Ig binding domains linked to each other.

3. The Ig binding protein according to claim 2, wherein the protein is a homo-multimer or a hetero-multimer.

4. The Ig binding protein according to claim 3, wherein one or more Ig binding domains are linked to each other directly or with one or more linkers.

5. The Ig binding protein according to claim 1, wherein said protein binds to IgG$_1$, IgG$_2$, IgG$_4$, IgM, IgA, Ig fragments, Fc fragments, or Fab fragments.

6. The Ig binding protein according to claim 1, wherein the protein is immobilized to a solid support.

7. An affinity separation matrix comprising the Ig binding protein according to claim 1 coupled to said affinity separation matrix.

8. A method of affinity purification of a protein comprising an Ig sequence, the method comprising:

(a) providing a liquid that contains protein comprising an Ig sequence;

(b) providing an affinity separation matrix according to claim 7;

(c) contacting said affinity separation matrix with the liquid under conditions that permit binding of the Ig binding protein to a protein comprising an Ig sequence; and (d) eluting said protein comprising an Ig sequence from said affinity purification matrix.

9. The method according to claim 8 wherein in step (d) wherein more than 90% of the protein comprising the Ig sequence is eluted from the Ig binding protein.

10. The method according to claim 8, further comprising (e) cleaning the affinity purification matrix with an alkaline cleaning liquid.

11. The method according to claim 10, wherein the Ig-binding capacity of the Ig binding protein after the cleaning step is at least 70% of its Ig binding capacity before the cleaning step.

12. The Ig binding protein of claim 1, wherein the Ig binding protein is stable under alkaline conditions of 0.5 M sodium hydroxide (NaOH) for at least 24 hours.

13. The Ig binding protein of claim 1, wherein relative to SEQ ID NO: 5, the Ig binding protein has an amino acid substitution at amino acid 9 or at amino acid 43.

14. The Ig binding protein of claim 12, wherein the one or more Ig binding domains comprise or consist of SEQ ID NO: 3, SEQ ID NO: 4, or a combination thereof.

\* \* \* \* \*

```
                          SEQUENCE LISTING

<160> NUMBER OF SEQ ID NOS: 19

<210> SEQ ID NO 1
<211> LENGTH: 58
<212> TYPE: PRT
<213> ORGANISM: Artificial Sequence
<220> FEATURE:
<223> OTHER INFORMATION: cs50

<400> SEQUENCE: 1

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Leu Ala Glu Ala
        35                  40                  45

Lys Lys Leu Asn Asp Ala Gln Ala Pro Pro
    50                  55

<210> SEQ ID NO 2
<211> LENGTH: 58
<212> TYPE: PRT
<213> ORGANISM: Artificial Sequence
<220> FEATURE:
<223> OTHER INFORMATION: Artificially synthesized cs52

<400> SEQUENCE: 2

Ile Asp Ala Lys Phe Asp Glu Ala Gln Gln Ala Ala Phe Tyr Glu Ile
```

-continued

```
1               5                    10                   15

Leu His Leu Pro Asn Leu Thr Glu Asp Gln Arg Asn Ala Phe Ile Gln
        20                   25                   30

Ser Leu Arg Asp Asp Pro Ser Thr Ser Leu Ser Leu Leu Ala Glu Ala
        35                   40                   45

Lys Lys Leu Asn Asp Ala Gln Ala Pro Pro
    50                   55

<210> SEQ ID NO 3
<211> LENGTH: 58
<212> TYPE: PRT
<213> ORGANISM: Artificial Sequence
<220> FEATURE:
<223> OTHER INFORMATION: Artificially synthesized cs58

<400> SEQUENCE: 3

Ile Asp Ala Lys Phe Asp Glu Ala Ala Gln Ala Ala Phe Tyr Glu Ile
1               5                    10                   15

Leu His Leu Pro Asn Leu Thr Glu Asp Gln Arg Asn Ala Phe Ile Gln
        20                   25                   30

Ser Leu Arg Asp Asp Pro Ser Val Ser Leu Ser Leu Leu Ala Glu Ala
        35                   40                   45

Lys Lys Leu Asn Asp Ala Gln Ala Pro Pro
    50                   55

<210> SEQ ID NO 4
<211> LENGTH: 58
<212> TYPE: PRT
<213> ORGANISM: Artificial Sequence
<220> FEATURE:
<223> OTHER INFORMATION: Artificially synthesized cs59

<400> SEQUENCE: 4

Ile Asp Ala Lys Phe Asp Glu Ala Gln Gln Ala Ala Phe Tyr Glu Ile
1               5                    10                   15

Leu His Leu Pro Asn Leu Thr Glu Asp Gln Arg Asn Ala Phe Ile Gln
        20                   25                   30

Ser Leu Arg Asp Asp Pro Ser Val Ser Leu Ala Leu Leu Ala Glu Ala
        35                   40                   45

Lys Lys Leu Asn Asp Ala Gln Ala Pro Pro
    50                   55

<210> SEQ ID NO 5
<211> LENGTH: 58
<212> TYPE: PRT
<213> ORGANISM: Artificial Sequence
<220> FEATURE:
<223> OTHER INFORMATION: Artificially synthesized cs60

<400> SEQUENCE: 5

Ile Asp Ala Lys Phe Asp Glu Ala Ala Gln Ala Ala Phe Tyr Glu Ile
1               5                    10                   15

Leu His Leu Pro Asn Leu Thr Glu Asp Gln Arg Asn Ala Phe Ile Gln
        20                   25                   30

Ser Leu Arg Asp Asp Pro Ser Val Ser Leu Ala Leu Leu Ala Glu Ala
        35                   40                   45

Lys Lys Leu Asn Asp Ala Gln Ala Pro Pro
    50                   55

<210> SEQ ID NO 6
```

-continued

```
<211> LENGTH: 58
<212> TYPE: PRT
<213> ORGANISM: Artificial Sequence
<220> FEATURE:
<223> OTHER INFORMATION: Artificially synthesized cs51

<400> SEQUENCE: 6

Ile Asp Ser Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Leu Gly Glu Ala
        35                  40                  45

Lys Lys Leu Asn Asp Ala Gln Ala Pro Pro
    50                  55

<210> SEQ ID NO 7
<211> LENGTH: 58
<212> TYPE: PRT
<213> ORGANISM: Artificial Sequence
<220> FEATURE:
<223> OTHER INFORMATION: Artificially synthesized cs56

<400> SEQUENCE: 7

Ile Asp Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Gly Glu Ala
        35                  40                  45

Lys Lys Leu Asn Glu Ser Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: Artificially synthesized cs54

<400> SEQUENCE: 8

Ile Asp Ala Gln His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Ala Glu Ala
        35                  40                  45

Lys Lys Leu Asn Glu Ser Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Artificially synthesized cs57

<400> SEQUENCE: 9

Ile Ala Ala Lys His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30
```

```
Ser Leu Arg Asp Asp Pro Ser Val Ser Leu Glu Ile Leu Gly Glu Ala
        35                  40                  45

Lys Lys Leu Asn Asp Ser Gln Ala Pro Lys
        50                  55

<210> SEQ ID NO 10
<211> LENGTH: 58
<212> TYPE: PRT
<213> ORGANISM: Artificial Sequence
<220> FEATURE:
<223> OTHER INFORMATION: Artificially synthesized cs55

<400> SEQUENCE: 10

Ile Ala Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
        20                  25                  30

Ser Leu Arg Asp Asp Pro Ser Val Ser Leu Glu Ile Leu Gly Glu Ala
        35                  40                  45

Lys Lys Leu Asn Asp Ser Gln Ala Pro Lys
        50                  55

<210> SEQ ID NO 11
<211> LENGTH: 116
<212> TYPE: PRT
<213> ORGANISM: Artificial Sequence
<220> FEATURE:
<223> OTHER INFORMATION: Artificially synthesized cs58 dimer

<400> SEQUENCE: 11

Ile Asp Ala Lys Phe Asp Glu Ala Ala Gln Ala Ala Phe Tyr Glu Ile
1               5                   10                  15

Leu His Leu Pro Asn Leu Thr Glu Asp Gln Arg Asn Ala Phe Ile Gln
        20                  25                  30

Ser Leu Arg Asp Asp Pro Ser Val Ser Leu Ser Leu Leu Ala Glu Ala
        35                  40                  45

Lys Lys Leu Asn Asp Ala Gln Ala Pro Pro Ile Asp Ala Lys Phe Asp
        50                  55                  60

Glu Ala Ala Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Ser Leu Leu Ala Glu Ala Lys Lys Leu Asn Asp Ala
            100                 105                 110

Gln Ala Pro Pro
        115

<210> SEQ ID NO 12
<211> LENGTH: 116
<212> TYPE: PRT
<213> ORGANISM: Artificial Sequence
<220> FEATURE:
<223> OTHER INFORMATION: Artificially synthesized cs59 dimer

<400> SEQUENCE: 12

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
        20                  25                  30
```

-continued

```
Ser Leu Arg Asp Asp Pro Ser Val Ser Leu Ala Leu Leu Ala Glu Ala
        35                  40                  45

Lys Lys Leu Asn Asp Ala Gln Ala Pro Pro Ile Asp Ala Lys Phe Asp
    50                  55                  60

Glu Ala Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Ala Leu Leu Ala Glu Ala Lys Lys Leu Asn Asp Ala
                100                 105                 110

Gln Ala Pro Pro
        115

<210> SEQ ID NO 13
<211> LENGTH: 116
<212> TYPE: PRT
<213> ORGANISM: Artificial Sequence
<220> FEATURE:
<223> OTHER INFORMATION: Artificially synthesized cs60 dimer

<400> SEQUENCE: 13

Ile Asp Ala Lys Phe Asp Glu Ala Ala Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro Ile Asp Ala Lys Phe Asp
    50                  55                  60

Glu Ala Ala Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Ala Leu Leu Ala Glu Ala Lys Lys Leu Asn Asp Ala
                100                 105                 110

Gln Ala Pro Pro
        115

<210> SEQ ID NO 14
<211> LENGTH: 117
<212> TYPE: PRT
<213> ORGANISM: Artificial Sequence
<220> FEATURE:
<223> OTHER INFORMATION: Artificially synthesized cs50 dimer

<400> SEQUENCE: 14

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
                20                  25                  30

Ser Leu Arg Asp Asp Pro Ser Val Ser Leu Ser Leu Leu Ala Glu Ala
        35                  40                  45

Lys Lys Leu Asn Asp Ala Gln Ala Pro Pro Ile Asp Ala Lys Phe Asp
    50                  55                  60

Glu Ala Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95
```

```
Ser Val Ser Leu Ser Leu Leu Ala Glu Ala Lys Lys Leu Asn Asp Ala
            100                 105                 110

Gln Ala Pro Pro Cys
        115

<210> SEQ ID NO 15
<211> LENGTH: 290
<212> TYPE: PRT
<213> ORGANISM: Artificial Sequence
<220> FEATURE:
<223> OTHER INFORMATION: Artificially synthesized cs50 pentamer

<400> SEQUENCE: 15

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Leu Ala Glu Ala
        35                  40                  45

Lys Lys Leu Asn Asp Ala Gln Ala Pro Pro Ile Asp Ala Lys Phe Asp
    50                  55                  60

Glu Ala Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
            85                  90                  95

Ser Val Ser Leu Ser Leu Leu Ala Glu Ala Lys Lys Leu Asn Asp Ala
            100                 105                 110

Gln Ala Pro Pro Ile Asp Ala Lys Phe Asp Glu Ala Gln Gln Ala Ala
        115                 120                 125

Phe Tyr Glu Ile Leu His Leu Pro Asn Leu Thr Glu Asp Gln Arg Asn
        130                 135                 140

Ala Phe Ile Gln Ser Leu Arg Asp Asp Pro Ser Val Ser Leu Ser Leu
145                 150                 155                 160

Leu Ala Glu Ala Lys Lys Leu Asn Asp Ala Gln Ala Pro Pro Ile Asp
                165                 170                 175

Ala Lys Phe Asp Glu Ala Gln Gln Ala Ala Phe Tyr Glu Ile Leu His
            180                 185                 190

Leu Pro Asn Leu Thr Glu Asp Gln Arg Asn Ala Phe Ile Gln Ser Leu
            195                 200                 205

Arg Asp Asp Pro Ser Val Ser Leu Ser Leu Leu Ala Glu Ala Lys Lys
        210                 215                 220

Leu Asn Asp Ala Gln Ala Pro Pro Ile Asp Ala Lys Phe Asp Glu Ala
225                 230                 235                 240

Gln Gln Ala Ala Phe Tyr Glu Ile Leu His Leu Pro Asn Leu Thr Glu
                245                 250                 255

Asp Gln Arg Asn Ala Phe Ile Gln Ser Leu Arg Asp Asp Pro Ser Val
            260                 265                 270

Ser Leu Ser Leu Leu Ala Glu Ala Lys Lys Leu Asn Asp Ala Gln Ala
        275                 280                 285

Pro Pro
    290

<210> SEQ ID NO 16
<211> LENGTH: 170
<212> TYPE: PRT
<213> ORGANISM: Artificial Sequence
```

-continued

```
<220> FEATURE:
<223> OTHER INFORMATION: Artificially synthesized cs59 pentamer

<400> SEQUENCE: 16

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ala Leu Leu Ala Glu Ala
        35                  40                  45

Lys Lys Leu Asn Asp Ala Gln Ala Pro Pro Ile Asp Ala Lys Phe Asp
    50                  55                  60

Glu Ala Gln Gln Ala Ala Phe Tyr Glu Ile Leu His Leu Pro Asn Leu
65                  70                  75                  80

Thr Glu Asp Gln Arg Asn Ala Phe Ile Gln Ser Leu Arg Asp Asp Pro
                85                  90                  95

Ser Val Ser Leu Ala Leu Leu Ala Glu Ala Lys Lys Leu Asn Asp Ala
            100                 105                 110

Gln Ala Pro Pro Ile Asp Ala Lys Phe Asp Glu Ala Gln Gln Ala Ala
        115                 120                 125

Phe Tyr Glu Ile Leu His Leu Pro Asn Leu Thr Glu Asp Gln Arg Asn
    130                 135                 140

Ala Phe Ile Gln Ser Leu Arg Asp Asp Pro Ser Val Ser Leu Ala Leu
145                 150                 155                 160

Leu Ala Glu Ala Lys Lys Leu Asn Asp Ala
                165                 170

<210> SEQ ID NO 17
<211> LENGTH: 58
<212> TYPE: PRT
<213> ORGANISM: Artificial Sequence
<220> FEATURE:
<223> OTHER INFORMATION: Artificially synthesized consensus sequence 1
<220> FEATURE:
<221> NAME/KEY: variant
<222> LOCATION: (3)..(3)
<223> OTHER INFORMATION: may be replaced by S
<220> FEATURE:
<221> NAME/KEY: variant
<222> LOCATION: (9)..(9)
<223> OTHER INFORMATION: may be replaced by A
<220> FEATURE:
<221> NAME/KEY: variant
<222> LOCATION: (40)..(40)
<223> OTHER INFORMATION: may be replaced by T
<220> FEATURE:
<221> NAME/KEY: variant
<222> LOCATION: (43)..(43)
<223> OTHER INFORMATION: may be replaced by A
<220> FEATURE:
<221> NAME/KEY: variant
<222> LOCATION: (46)..(46)
<223> OTHER INFORMATION: may be replaced by G

<400> SEQUENCE: 17

Ile Asp Ala Lys Phe Asp Glu Ala Gln Gln Ala Ala Phe Tyr Glu Ile
1               5                   10                  15

Leu His Leu Pro Asn Leu Thr Glu Asp Gln Arg Asn Ala Phe Ile Gln
            20                  25                  30

Ser Leu Arg Asp Asp Pro Ser Val Ser Leu Ser Leu Leu Ala Glu Ala
        35                  40                  45

Lys Lys Leu Asn Asp Ala Gln Ala Pro Pro
    50                  55
```

```
<210> SEQ ID NO 18
<211> LENGTH: 58
<212> TYPE: PRT
<213> ORGANISM: Artificial Sequence
<220> FEATURE:
<223> OTHER INFORMATION: Artificially synthesized consensus sequence 2
<220> FEATURE:
<221> NAME/KEY: variant
<222> LOCATION: (2)..(2)
<223> OTHER INFORMATION: may be replaced by A
<220> FEATURE:
<221> NAME/KEY: variant
<222> LOCATION: (4)..(4)
<223> OTHER INFORMATION: may be replaced by Q
<220> FEATURE:
<221> NAME/KEY: variant
<222> LOCATION: (7)..(7)
<223> OTHER INFORMATION: may be replaced by k
<220> FEATURE:
<221> NAME/KEY: variant
<222> LOCATION: (40)..(40)
<223> OTHER INFORMATION: may be replaced by V
<220> FEATURE:
<221> NAME/KEY: variant
<222> LOCATION: (46)..(46)
<223> OTHER INFORMATION: may be replaced by A
<220> FEATURE:
<221> NAME/KEY: variant
<222> LOCATION: (53)..(53)
<223> OTHER INFORMATION: may be replaced by D

<400> SEQUENCE: 18

Ile Asp Ala Lys His Asp Glu Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Gln Ser Leu Glu Ile Leu Gly Glu Ala
        35                  40                  45

Lys Lys Leu Asn Glu Ser Gln Ala Pro Lys
    50                  55

<210> SEQ ID NO 19
<211> LENGTH: 58
<212> TYPE: PRT
<213> ORGANISM: Artificial Sequence
<220> FEATURE:
<223> OTHER INFORMATION: Artificially synthesized reference 2

<400> SEQUENCE: 19

Ile Ala Ala Gln His Asp Lys Asp Gln Gln Ala Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Arg Asp Asp Pro Ser Val Ser Leu Glu Ile Leu Ala Glu Ala
        35                  40                  45

Lys Lys Leu Asn Asp Ala Gln Ala Pro Lys
    50                  55
```